United States Patent [19]
Gzybowski et al.

[11] Patent Number: 6,129,086
[45] Date of Patent: Oct. 10, 2000

[54] EAR PRESSURE EQUALIZER

[76] Inventors: Michael S. Gzybowski, P.O. Box 13381, Fort Wayne, Ind. 46868-3381; Mark S. Boudreau, 8713 Gateshead Rd., Alexandria, Va. 22309

[21] Appl. No.: 09/048,396

[22] Filed: Mar. 26, 1998

[51] Int. Cl.[7] .............................. A61F 11/06; A63B 23/18
[52] U.S. Cl. ............................................. 128/867; 482/13
[58] Field of Search ..................... 128/200.24, 202.13, 128/202.16, 207.14, 207.15, 207.16, 864, 867; 482/13; 446/202; D24/110; 181/130

[56] References Cited

U.S. PATENT DOCUMENTS

| | | | |
|---|---|---|---|
| 2,681,055 | 6/1954 | Gowland | 446/202 |
| 3,958,565 | 5/1976 | Wright | 482/13 X |
| 4,770,413 | 9/1988 | Green | 482/13 |
| 4,854,574 | 8/1989 | Larson et al. | 482/13 |
| 4,929,181 | 5/1990 | Undlin | 446/202 X |
| 4,973,047 | 11/1990 | Norell | 482/13 |
| 5,467,784 | 11/1995 | Mobley et al. | 128/864 X |

*Primary Examiner*—Michael A. Brown
*Assistant Examiner*—Denise Pothier
*Attorney, Agent, or Firm*—Michael S. Gzybowski

[57] ABSTRACT

A device for regulating pressure which can be used to relieve discomfort caused by inner ear pressure. The device includes a hollow body having an open end, a movable member within the hollow body which defines a first chamber that extends between the movable member and the open end of the hollow body, and various alternative structural elements which regulate pressure in the first chamber. To relieve discomfort caused by inner ear pressure, the open end of the hollow body is provided with a mouthpiece. A person experiencing discomfort caused by inner ear pressure, blows through or sucks on the mouthpiece, causing a change in pressure in the first chamber. The device regulates pressure in the first chamber in such a way to help relieve the person's inner ear pressure.

13 Claims, 5 Drawing Sheets

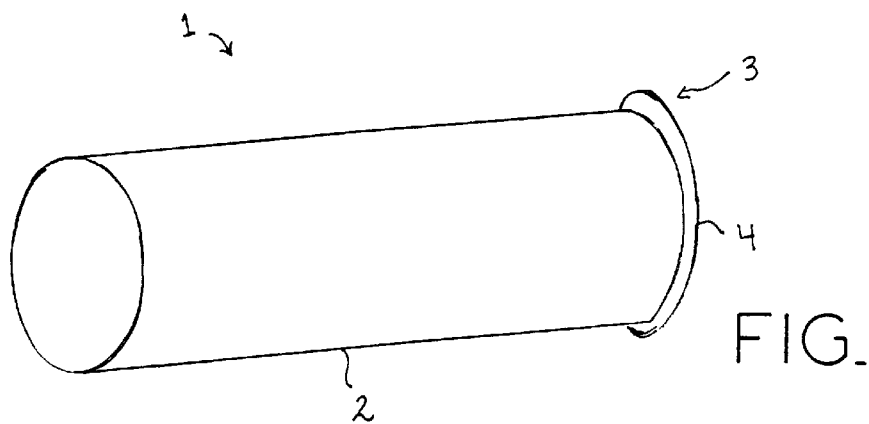
FIG_1
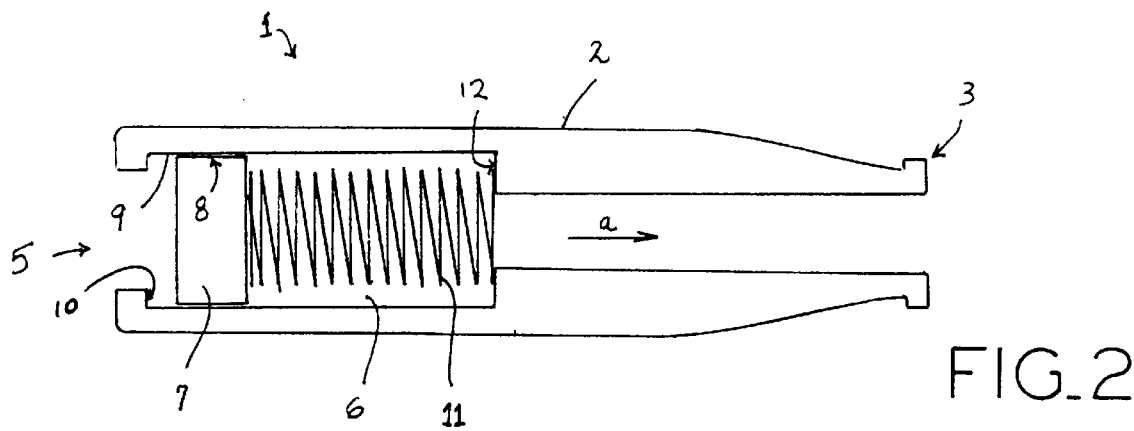
FIG_2
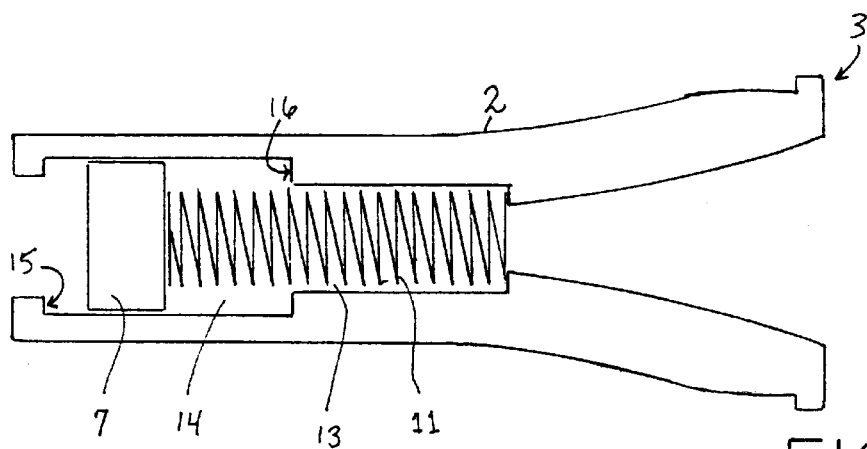
FIG_3

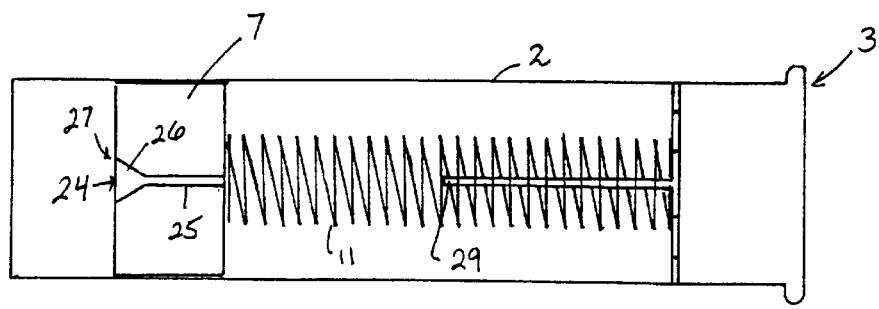
FIG_7A
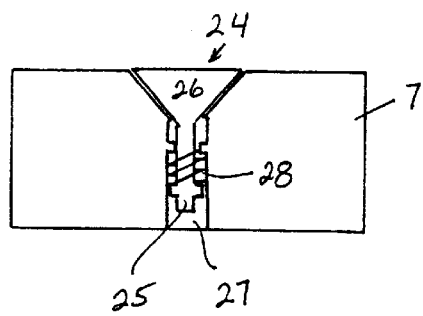
FIG_7B
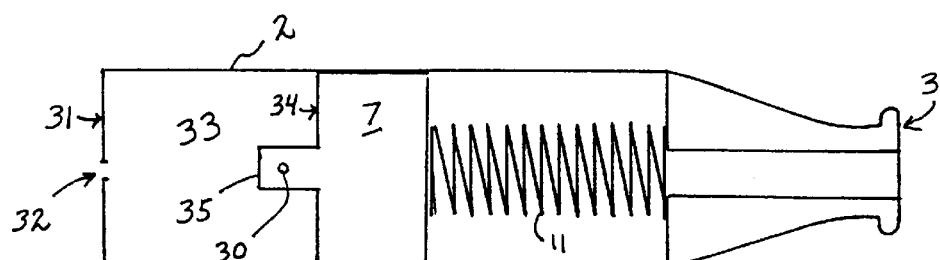
FIG_8
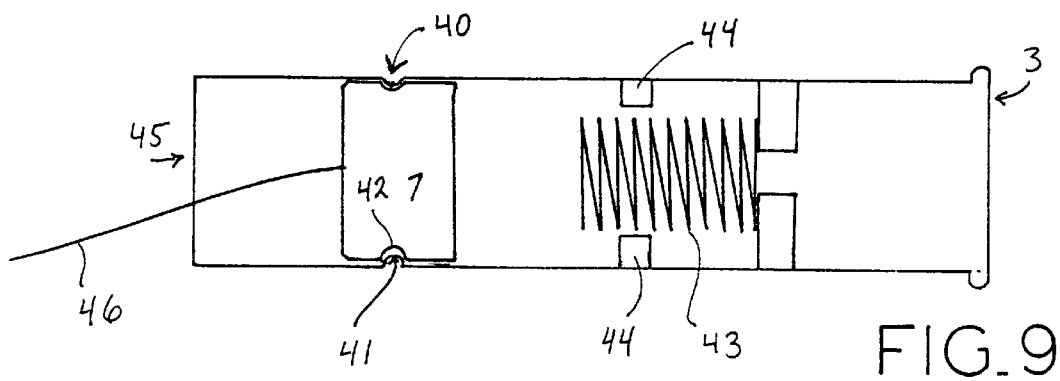
FIG_9

EAR PRESSURE EQUALIZER

TECHNICAL FIELD

The present invention relates to methods and apparatus for relieving pressure differences in a person's inner ear. More particularly, the present invention is directed to mouth operated devices which can help relieve pressure differences in a person's inner ear.

BACKGROUND ART

Many people find it difficult to equalize the pressure in their inner ears when they experience ambient pressure changes. Such changes of ambient pressures are most commonly encountered during the ascension and descension of aircraft. Often during such ascension and descension ambient pressure changes rapidly while the pressure inside a person's inner ear does not change. The resulting pressure difference between the person's inner ear and the ambient can become uncomfortable and eventually painful as the pressure difference increases. For persons suffering from sinus problems, such pressure differences between the inner ear and ambient can result in prolonged problems if pressure equalization is not achieved in a short time.

More common ways of equalizing pressure in the inner ear include swallowing and chewing gum. The problem with such measures is that they generally are not effective for small children, and too often are not effective for adults as well.

The present invention provides methods and apparatus which make it easy for persons experiencing pressure differences in their inner ears to relieve such pressure differences safely, and effectively.

DISCLOSURE OF THE INVENTION

It is accordingly one object of the present invention to provide a number of devices for relieving pressure differences within a person's inner ear.

Another object of the present invention is to provide devices which will equalize pressure differences between a person's inner ear and the ambient environment of the person.

It is another object of the present invention to provide simple to operate mechanical devices which can be used to relieve pressure differences in a person's inner ear.

It is another object of the present invention to provide mouth operated devices which can be used to relieve pressure differences in a person's inner ear.

A further object of the present invention is to provide mouth operated mechanical devices which can be used to relieve pressure differences in a person's inner ear.

A further object of the present invention is to provide a number of methods for relieving pressure differences in a person's inner ear.

It is a further object of the present invention to provide methods for equalizing pressure differences within a person's inner ear and the ambient environment.

According to these and further objects of the present invention which will become apparent as the description hereafter proceeds, the present invention provides a device for relieving inner ear pressure which includes:

a hollow elongate body having a mouthpiece on a first end thereof;

a movable member located in the hollow elongate body and defining a movable wall of a first chamber that extends between the movable member and the mouthpiece, movement of the movable member in the hollow elongate body being effected by pressure changes in the first chamber; and means for regulating pressure in the first chamber when a person applies a pressure change to the first chamber through the mouthpiece.

The present invention further provides a device for relieving inner ear pressure which includes:

a first hollow body member having a mouthpiece on one end;

a second body member telescopically coupled to the first hollow body member and having a wall which defines a wall of a chamber within the first hollow body member; and a detent mechanism which cooperates between the first hollow body member and the second body member to secure the relative positions therein until a pressure change occurs in the chamber.

The present invention further provides a method of relieving inner ear pressure which involves:

providing an hollow elongate member having a mouthpiece on one end, a movable member that is received therein and defines a first chamber that extends between the movable member and the mouthpiece, and means for regulating pressure in the first chamber when a person applies a pressure change to the first chamber through the mouthpiece;

positioning the mouthpiece in the mouth of a person experiencing a pressure difference between their inner ear pressure and ambient pressure;

having the person apply a pressure change to the first chamber through the mouthpiece; and allowing the means for regulating pressure in the first chamber regulate the pressure therein to thereby relieve the pressure difference between the person's inner ear pressure and the ambient pressure.

The present invention also provides a device for regulating pressure which comprises:

a hollow body having an open end;

a movable member located in the hollow body and defining a movable wall of a chamber that extends between the movable member and the open end, wherein movement of the movable body within the hollow body is effected by pressure changes in the chamber; and means for regulating pressure in the first chamber when a pressure change is applied to the chamber through the open end, the means for regulating pressure comprising structure which controls movement of the movable member.

BRIEF DESCRIPTION OF DRAWINGS

The present invention will be described with reference to the attached drawings which are provided as non-limiting examples which depict various features of the present invention, in which:

FIG. 1 is a perspective view of a device for relieving inner ear pressure according to one embodiment of the present invention.

FIG. 2 is a longitudinal cross-sectional view of the device of FIG. 1 according to one embodiment.

FIG. 3 is a longitudinal cross-sectional view of the device of FIG. 1 according to another embodiment.

FIG. 7a depicts an alternative embodiment of the device of the present invention in which the shuttle is provided with a spring biased valve element.

FIG. 7b depicts an embodiment of the spring biased valve element of FIG. 7a in cross-section.

FIG. 8 depicts an alternative embodiment of the present invention which is designed to automatically release, thereby limiting pressure (vacuum) applied to the rear side of the shuttle.

FIG. 9 depicts an embodiment of the device which includes a detent structure or mechanism that temporarily holds the shuttle in position.

BEST MODE FOR CARRYING OUT THE INVENTION

Figure 4:
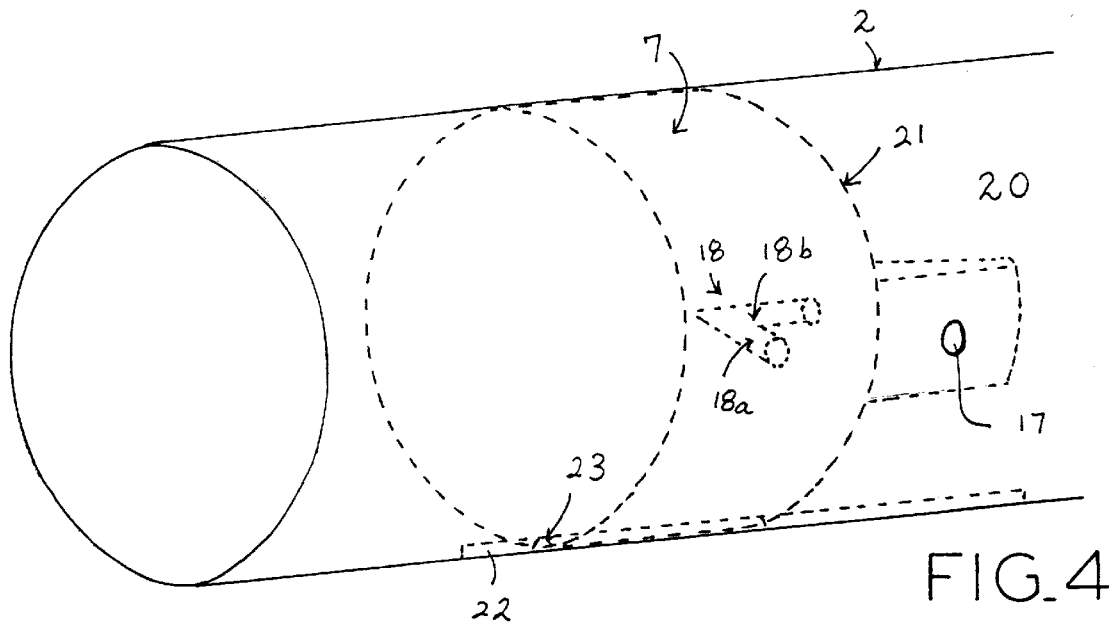
FIG. 4 is a perspective broken view of a device for relieving inner ear pressure according to another embodiment of the present invention which depicts the positioning of the shuttle when the device is in its normal unpressurized state.

The present invention is directed to devices and methods which can be used to relieve pressure differences experienced by persons in their inner ears. Such pressure differences are relieved by reducing the difference between the pressure within a person's inner ear and the ambient pressure. When a person is seated in an ascending airplane, the ambient pressure may decrease, resulting in the person's inner ear pressure becoming larger than the ambient pressure. On the other hand, a person seated in a descending airplane may experience an increase in ambient pressure, resulting in the person's inner ear pressure becoming smaller that ambient pressure. In each instance the difference in pressure between the person's inner ear and the ambient can cause discomfort.

Ideally, the devices of the present invention fully equalize the pressure difference between a person's inner ear and the ambient environment. However, a person experiencing discomfort from such pressure differences can often experience relief if the pressure difference is merely reduced. Accordingly, the devices and methods of the present invention are referred to as either relieving pressure differences or equalizing pressure differences.

The devices of the present invention are manually operated devices which include structure that assists persons using the devices to effect an increase in pressure difference between the cavities in their mouths and pressures in their inner ear. Creating such differences in pressure has been found to effectively cause the inner ear cavities to "open" and experience pressure equalization with the ambient environment. It is noted that the term pressure encompasses vacuums inasmuch as vacuums are either negative pressures or relatively lower pressures.

The devices of the present invention are designed to assist the user in gradually increasing the pressure difference between their mouth cavity and inner ear. In this regard, the devices include structure which both effects the rate at which pressure increases are effected and means which limit the pressure increases. Further embodiments of the present invention include structure which relieves the pressure differences created thereby. Such structure may gradually relieve the pressure differences after a period of time, or according to some embodiments, may effect an abrupt relief of pressure.

The devices of the present invention have mouthpiece portions by which the devices are received in the mouth of a user. The mouthpiece portions may be of any convenient design. For adults, the mouthpiece portions may comprise merely a cylindrical portion at one end of the devices. For children the mouthpieces may be tapered or more flat, like the shape of mouthpieces which are commonly found on toy whistles, bubble pipes, musical instruments, and the like.

When the devices of the present invention are made small, they should be provided with means for preventing them from being swallowed or for preventing the user from choking on the devices. Such means may include a blocking structure similar to that found on infant pacifiers which prevents the pacifiers from being placed completely into an infant's mouth. Other means may simply include strings, cords, or other tethers which are attached to the devices.

FIG. 1 is a perspective view of a device for relieving inner ear pressure according to one embodiment of the present invention. As depicted in FIG. 1 the device 1 includes an elongated body 2 having a mouthpiece 3 on one end thereof. According to the embodiment depicted in FIG. 1, the elongated body 2 has a cylindrical shape. Other shapes, particularly those having non-circular cross-sections can be used for the elongated body 2. Examples include, but are not limited to, bodies with oval cross-sectional shapes, square or rectangular cross-sectional shapes, flattened circular or flattened oval cross-sectional shapes, egg cross-sectional shapes, etc. As discussed below, the elongated body 2 includes a sliding structure (shuttle 7). Thus, the elongated shape of the body 2 facilitates movement the sliding structure, However, other than including a straight or linear segment or portion of the body which facilitates the movement of the sliding structure as discussed below, the overall shape of elongated body 2 does not have to be limited to a straight or linear shape. For example, in place of the elongated body 2 depicted in FIG. 1, an "L"-shaped body or a body having a curved or bent shape could be utilized. These and other non-linear shapes would allow alternative positioning of the elements discussed below, such as placing the sliding structure in a more visible or viewable portion of the body so that the user can watch movement thereof as the device is being used. Being able to watch the device operate, i.e. watch movement of the sliding structure, may be appealing to children. Likewise, including an air driven spinning structure, similar to a pin wheel in the device or a structure which makes a sound as a result of airflow through the devices may make the devices more appealing for children to use.

The mouthpiece 3 depicted in FIG. 1 is merely a cylindrical end portion of elongated body 2 which can include a small rib 4 that a persons lips or teeth can catch. Other mouthpiece shapes are depicted in others of the figures. The mouthpieces can be of any convenient shape. However, it has been determined that large diameter mouthpieces tend to cause a person's jaw to be opened more. This positioning of the jaw can assist in equalizing pressure in a person's inner ear. Accordingly, mouthpieces with a diameter that will cause a person's mouth to open at about 40 percent of maximum (unassisted) or greater, or about 50 percent or maximum (unassisted) can be particularly useful in helping relieve inner ear pressure. For example, mouthpieces that have a diameter of about 1 to about 1.5 inches are generally suitable for adults, whereas mouthpieces that have a diameter of about 0.5 to about 0.7 inches are generally suitable for children.

FIG. 2 is a longitudinal cross-sectional view of the device of FIG. 1 according to one embodiment. As depicted in FIG. 2, the device 1 includes elongated body 2 which includes a central through-bore 5. The through-bore 5 includes an enlarged stepped portion 6 in which a shuttle 7 is positioned. Shuttle 7 has a cross-sectional shape which is complementary to the cross-sectional shape of the enlarged stepped bore portion 6 and is dimensioned to freely slide within enlarged stepped bore portion 6 along the axis thereof. Shuttle 7 is sufficiently sized to provide a seal between its outer peripheral surface 8 and the inner surface 9 of enlarged stepped bore portion 6, so that movement of the shuttle 7 can be effected by pressure differences on opposite axial sides of the shuttle 7. In alternative embodiments, the shuttle 7 can merely include a flange or flared peripheral edge adjacent one or both ends thereof which seal(s) against the inner surface 9 of the enlarged stepped bore portion 6. Otherwise, a seal such as an o-ring could be provided in a groove on the peripheral surface 8 of the shuttle 7 and used to allow pressure differences to exist on opposite axial sides of the shuttle 7.

The forward end 10 of enlarged stepped bore portion 6 limits forward movement of shuttle 7. Rearward movement of the shuttle 7 towards mouthpiece 3 (note tapered shape) is limited by spring member 11. As depicted, spring member 11 extends between the rear of shuttle 7 and the rearward end 12 of the enlarged stepped bore portion 6. Spring member 11 provides a biasing force which resists rearward movement of shuttle 7 along the direction of arrow "a." Spring member 11 has a spring constant which effects a gradual resistance to rearward movement of shuttle 7 as it continues in the rearward direction.

In use, mouthpiece 3 of the device 1 is placed in the mouth of a person who is experiencing inner ear discomfort due to ambient and inner ear pressure differences. The person sucks on the mouthpiece 3 to create a pressure (vacuum) on the rearward side of shuttle 7. In response to the pressure (vacuum), shuttle 7 moves rearward in the direction of arrow "a." As shuttle moves rearward, it experiences increased resistance to movement by force of spring member 11. As a result, the person utilizing the device has to increase suction on the device in order to move shuttle 7 rearward. When or before shuttle 7 fully compresses spring 11, the pressure (vacuum) created in the user's mouth effects inner ear pressure relief or equalization.

The elongated body 2 and shuttle 7 can be made from any suitable material including metals and plastics. If the elongated body 2 is made from a clear or transparent plastic material, the user can visually observe the position of the shuttle 7. The spring member 11 can be made out of any suitable material such as spring steel. If the device 1 is designed to be used once and discarded, the spring member 11 can be made from a material such as a low grade steel which may be susceptible to corrosion.

FIG. 3 is a longitudinal cross-sectional view of the device of FIG. 2 according to another embodiment. In the embodiment of the device depicted in FIG. 3 the spring member 11 is located in a stepped bore portion 13 which is adjacent to the stepped bore portion 14 in which shuttle 7 moves longitudinally. In this embodiment, both the front end 15 and rear end 16 of stepped bore portion 14 limit the longitudinal movement of shuttle 7. Rather than limiting the rearward movement of shuttle 7, spring member 11 is compressed by movement of shuttle 7 into stepped bore portion 13.

FIG. 4 is a perspective broken view of a device for relieving inner ear pressure according to another embodiment of the present invention which depicts the positioning of the shuttle when the device is in its normal unpressurized state. The device 1 in FIG. 4 includes an elongated body 2 having a shuttle 7 which is movable within the elongated body 2. The movement of the shuttle 7 within the elongated body 2 can be limited by the stepped bore structure depicted in either FIGS. 2 or 3, or by continuous or discrete abutments which extend inwardly from the inner wall of the elongate body 2. In an alternative embodiment, spring member 11 can be attached at one end to shuttle 7 and coupled to the inside of the elongated body 2 at the other end. In this manner, the spring member 11 could both limit the forward position of the shuttle 7 when the spring member 11 is extended and limit the rearward position of the shuttle 7 when the spring member 11 is compressed by the shuttle 7.

The device of FIG. 4 is designed to automatically release, thereby limiting, pressure (vacuum) applied to the rear side of the shuttle 7. This is accomplished by providing at least one aperture 17 through the side of the elongated body 2 and a passageway 18 through shuttle 7. The passageway 18 can be aligned with aperture 17 and thereby provide fluid communication between the ambient environment (pressure) and the space or chamber 20 within the elongated body 2 which is behind the rear side of the shuttle 7.

As depicted in FIG. 4, the shuttle 7 includes a passageway 18 which includes a radial portion 18a that is connected to an axial portion 18b which extends through the rear side 21 of shuttle 7. The radial portion 18a of passageway 18 extends through the peripheral side of shuttle 7 and is longitudinally aligned with aperture 17. The necessary alignment between the shuttle 7 and elongated body 2 can be achieved by providing a key way structure between the shuttle 7 and inside surface of the elongated body 2. For an elongated body 2 with a circular cross-sectional area, a suitable key way can include an inward directed projection 22 on the inner surface of the elongated body 2 and a corresponding slot 23 formed in the side of the shuttle 7. The projection 22 can include an abutment structure which limits the longitudinal movement of shuttle 7 in the rearward direction at a position where radial portion 18a of passageway 18 aligns with aperture 17. It is understood that the key way projection could be provided in the inner side wall of the elongated body 2 and the shuttle 7 could be provided with an outward directed projection. The use of a key way is not required if the elongated body 2 and shuttle 7 have cross-sectional shapes, e.g. square, egg, oval shaped, flattened circle, etc. which prevent rotation of the shuttle 7 with respect to the elongated body 2. Otherwise, the spring member 11 could be attached at one end to the shuttle 7 and at the other end to the elongate body 2 and used to maintain the proper longitudinal alignment between the radial portion 18a of passageway 18 with aperture 17.

The shuttle 7 in FIG. 4 can be coupled to a spring member 11 as in FIGS. 2 and 3. In addition, the elongated body 2 of the embodiment of FIG. 4 can have the stepped bore portions of FIGS. 2 or 3.

As a person sucks on the mouthpiece (not shown), the shuttle 7 will move rearwardly against the force of spring member 11. Pressure (vacuum) continues to increase at the rear of shuttle 7 as the shuttle 7 moves rearward. Eventually shuttle 7 reaches a position at which the radial portion 18a of passageway 18 aligns with aperture 17. At this position, pressure (vacuum) which has increased at the rear of the shuttle 7 is abruptly released, causing relief or equalization of the user's inner ear pressure.

Figure 5A:
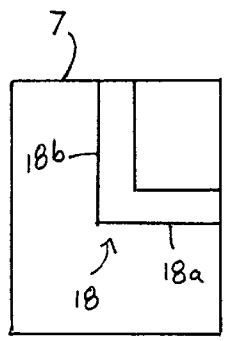
FIGS. 5a and 5b are cross-sectional views of different embodiments of the shuttle of FIG. 4 which depict different internal passageways in the shuttle.
Figure 5B:
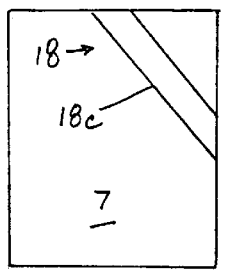

FIGS. 5a and 5b are cross-sectional views of different embodiments of the shuttle of FIG. 4 which depict different internal passageways in the shuttle. In both FIGS. 5a and 5b the shuttle 7 can have a cylindrical shape as depicted in FIG. 4. In FIG. 5a the passageway 18 includes a radial portion 18a and an axial portion 18b. The radial portion 18a of passageway 18 extends though the peripheral surface of the shuttle 7. The axial portion 18b can be centered with or off-center from the axial center of the shuttle 7. In FIG. 5b the passageway 18 has a single straight portion 18c which extends though the back and peripheral side of the shuttle 7 as depicted. It is to be understood that other configurations could be used for the passageway 18 as long as fluid communication is provided between the back of the shuttle 7 and the peripheral side. In addition, multiple passageways 18 could be used in combination with multiple apertures 18c.

Figure 6:
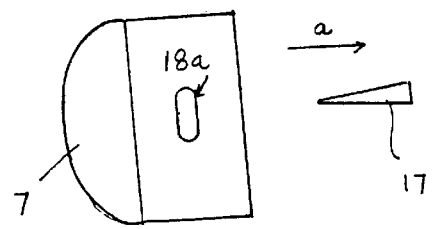
FIG. 6 depicts alternative configurations of the shuttle passageway and aperture of the elongate body that can be used with the device of FIG. 4.

FIG. 6 depicts alternative configurations of the shuttle passageway and aperture of the elongate body that can be used with the device of FIG. 4. The size of the passageway 18 will effect the rate or speed at which pressure (vacuum) behind shuttle 7 is released. For some persons, a quick or abrupt release of pressure (vacuum) behind the shuttle 7 more easily effects inner ear pressure relief or equalization. In an alternative embodiment depicted in FIG. 6, the opening of the radial portion 18a of the passageway 18 at the peripheral surface of shuttle 7 could have an elongated shape as depicted, and the aperture 17 in the side of elongated body 2 could have a wedged shape as depicted. In this embodiment, as the shuttle 7 moves rearward in the direction of arrow "a" the common opening between the radial portion 18a of passageway 18 and aperture 17 increases in size, thus varying the rate at which pressure (vacuum) behind the shuttle 7 is released.

FIG. 7a depicts an alternative embodiment of the device of the present invention in which the shuttle 7 is provided with a spring biased valve element 24. FIG. 7b depicts an embodiment of the spring biased valve element in cross-section. As depicted in FIG. 7a the spring biased valve element 24 includes a valve stem 25 and a valve head 26 which is received in a port 27 in a known manner. A valve spring 28 is provided to bias the valve element 24 in a closed position in a known manner.

In this embodiment, a valve actuating projection 29 is provided in the elongated body 2 in alignment with the spring biased valve element 24 as depicted. When a person sucks on mouthpiece 3, the shuttle 7 moves rearward until the valve actuating projection 29 contacts the end of valve stem 25 and pushes the spring biased valve element 24 into an open position. Once the spring biased valve element 24 opens, pressure (vacuum) behind the spring biased valve element 24 is released. This release in pressure (vacuum) can help a person relieve inner ear pressure and also limits the amount of pressure (vacuum) that can be built up behind the shuttle 7 and in a person's mouth.

It is to be understood that other types of biased valve elements could be used in the embodiment of the invention depicted in FIG. 7. For example, a flap valve, a reed valve, a ball valve, and similar valves could be used.

FIG. 8 depicts an alternative embodiment of the present invention which is designed to automatically release, thereby limiting pressure (vacuum) applied to the rear side of the shuttle. This is accomplished by providing at least one aperture 30 through the side of the elongated body 2 at a location whereat the front edge of shuttle 7 can pass when the shuttle 7 is drawn rearwardly as a person sucks on mouthpiece 3. In this embodiment, the distal end 31 of the elongated body 2 is sealed or otherwise provided with a small orifice 32 which allows a pressure (vacuum) to be created in the space or chamber 33 in the elongated body 2 which is between the front 34 of shuttle 7 and distal end 31 of the elongate body 2.

As a person sucks on mouthpiece 3, the shuttle 7 moves rearwardly against the force of spring member 11. Pressure (vacuum) continues to increase at the rear of shuttle 7 as the shuttle 7 moves rearward. At the same time, pressure (vacuum), which may be throttled by an orifice 32, builds up at the front of shuttle 7. Eventually shuttle 7 reaches a position at which the front edge of shuttle 7 passes aperture 30. At this point pressure (vacuum) in front of shuttle 7 is relived, thus allowing shuttle 7 to move rearward only against the force of spring member 11. In this embodiment, spring member 11 is only required to have a minimum force necessary to push shuttle 7 to its forward position. Accordingly, once pressure (vacuum) in front of shuttle 7 is relived, the shuttle 7 moves quickly rearward, effecting an abrupt pressure relief at the rear of shuttle 7, causing relief or equalization of the user's inner ear pressure.

In order to assist spring member 11 in pushing shuttle 7 to its forward position, a one-way valve can be positioned in the distal end 31 of elongated body 2 or in shuttle 7. The use of such one-way valve(s) will allow air in the space in the elongated body 2 which is between the front of shuttle 7 and distal end 31 to escape so that the force required by spring member 11 is minimized.

It is noted that the shuttle 7 can either have an overall length which provides a desired travel distance before it passes by aperture 30. Otherwise, shuttle 7 can be provided with a skirt or skirt portion 35 which extends the length of the shuttle 7. A similar skirt or skirt portion could be provided on the shuttle 7 in the embodiment of FIG. 4.

The elongated body 2 of the device in FIG. 8 can include the stepped bore shapes of FIGS. 2 or 3 or similar stepped bore shapes.

FIG. 9 depicts an embodiment of the device in which includes a detent structure or mechanism that temporarily holds the shuttle in position. In this embodiment, the shuttle 7 is provided with a detent structure or mechanism 40 that holds the shuttle 7 in a set position until a pressure (vacuum) is established between the shuttle 7 and the mouthpiece 3 of the device. The detent structure or mechanism 40 can include a continuous or discontinuous rib 41, or a single or plurality of projections that are formed on the inner surface of the elongate body 2 which are received in a corresponding groove 42 or indentation(s) on the peripheral surface of the shuttle 7. The rib or projections can be made from a resilient or elastic material or similar material that can yield when pressure is exerted on shuttle 7 so as to release the detent structure or mechanism 40. In other embodiments these elements could be reversed, so that for example, the rib 41 would be on the peripheral surface of the shuttle 7 and the groove 42 would formed in the inner surface of the elongate body 2. In other embodiments, the detent structure or mechanism 40 could include spring biased structures such as bearings that are received in a corresponding groove or indentions. Other known detent structures or mechanisms could also be used.

The detent structure or mechanism 40 holds the shuttle 7 in position as depicted in FIG. 9. When a person sucks on mouthpiece 3, a pressure (vacuum) is created on the space between shuttle 7 and the mouthpiece 3. Once this pressure (vacuum) reaches a certain magnitude, the detent structure or mechanism 40 releases the shuttle 7 and the shuttle 7 moves rapidly toward the mouthpiece 3. This release of pressure can help relieve a person's inner ear pressure.

As depicted, a spring member 43 can be provided to arrest the movement of the shuttle 7 toward the mouthpiece 3. In addition, an abutment structure 44 can be provided to stop the movement of the shuttle 7. The distal end 45 of the device is preferably open. A string, cord, chain or similar member 46 can be attached to the front of the shuttle 7 and used to pull the shuttle 7 into the position depicted in FIG. 9 in which position the detent structure or mechanism 40 engages and holds the shuttle 7 in position.

Figure 10:
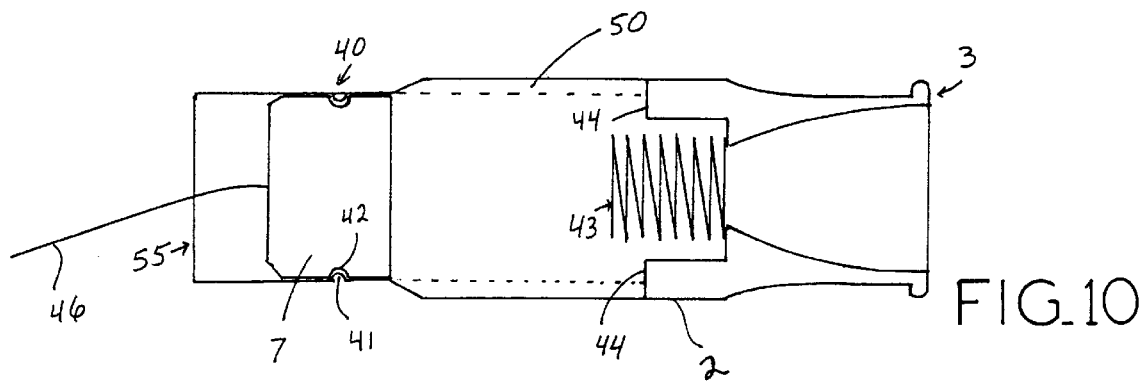
FIG. 10 depicts another embodiment of the device which includes a detent structure or mechanism that temporarily holds the shuttle in position.

FIG. 10 depicts another embodiment of the device in which includes a detent structure or mechanism that temporarily holds the shuttle in position. The embodiment of the device in FIG. 10 is substantially similar to that depicted in FIG. 9, except the elongate body 2 includes a wider section 50 between the position at which the shuttle 7 is held by the detent structure or mechanism 40 and the mouthpiece 3. In this embodiment, when the detent structure or mechanism 40 releases shuttle 7, and shuttle 7 passes into the wider section 50 of the elongate body 2, air can freely flow past the shuttle 7 from an opening in end 55 of the elongate body 2. Therefore, in operation, a person sucks on the mouthpiece 3 until a certain pressure (vacuum) is built up and the detent structure or mechanism 40 releases shuttle 7. Upon release, shuttle 7 passes into the wider section 50 of the elongate body 2 and thus creates an abrupt release of the built up pressure (vacuum). This creation and abrupt release of pressure (vacuum) helps relieve a person's inner ear pressure.

Figure 11:
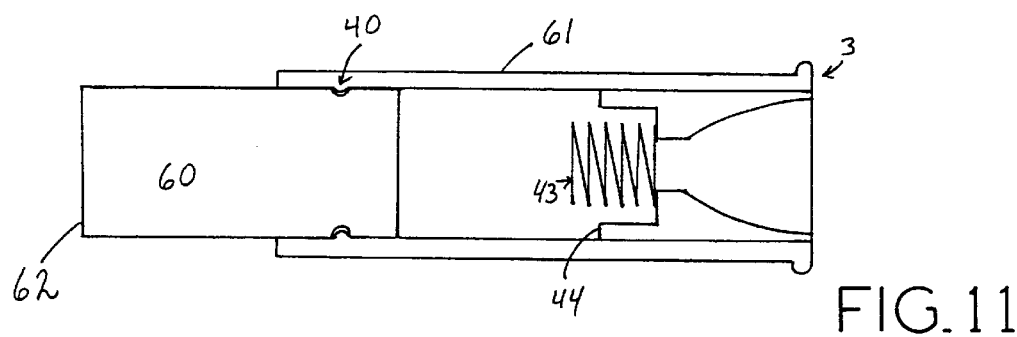
FIG. 11 depicts another embodiment of the device which includes a detent structure or mechanism that temporarily holds the shuttle in position.

FIG. 11 depicts another embodiment of the device in which includes a detent structure or mechanism that temporarily holds the shuttle in position. In FIG. 11 the shuttle 60 comprises an elongate structure which is telescopically received in elongate body 61. This embodiment of the invention allows a person to merely grab the distal end 62 of shuttle 60 and pull it away from elongate body 61 until the detent structure or mechanism 40 engages. This embodiment of the invention is actually collapsible and can be stored in its collapsed condition prior to use. The operation of this embodiment of the invention is similar to the operation of the embodiment depicted in FIG. 9, except rather than pull member 46 to reset the device, one merely grabs and pulls the shuttle 60.

Figure 12:
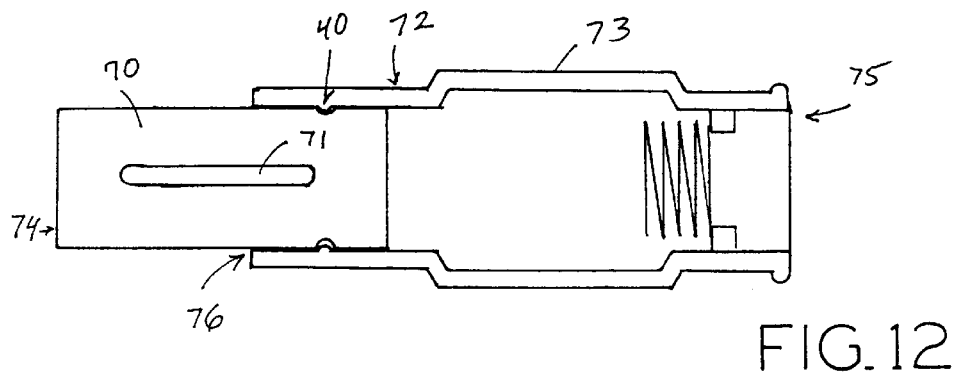
FIG. 12 depicts another embodiment of the device which includes a detent structure or mechanism that temporarily holds the shuttle in position.

FIG. 12 depicts another embodiment of the device in which includes a detent structure or mechanism that temporarily holds the shuttle in position. The device of FIG. 12 is substantially the same as the device of FIG. 11, except in FIG. 12 the shuttle 70 is provided with one or more axial grooves 71 in the peripheral surface thereof, and the elongate body 72 is provided with a wide portion 73 as in FIG. 10. The axial grooves 71 are positioned between the detent structure or mechanism 40 and the distal end 74 of the shuttle 70 as depicted so that when a person sucks on mouthpiece 75 and thereby causes detent structure or mechanism 40 to release shuttle 70, the axial grooves 71 provide fluid communication between the distal end 76 of elongate body 72 and the inner space within the wide portion 73. This fluid communication provides an abrupt release of pressure which assists in the relief of a person's inner ear pressure. The wide portion 73 of the elongate body 72 can be continuous, i.e. have the same cross-sectional shape as the narrow portion of the elongate body 72, or can comprise discrete wider portions that extend less than 360° of the circumference of the elongate body 72. Similarly, the wide portions of the embodiments of FIGS. 10 and 13 could be discrete or continuous.

Figure 13:
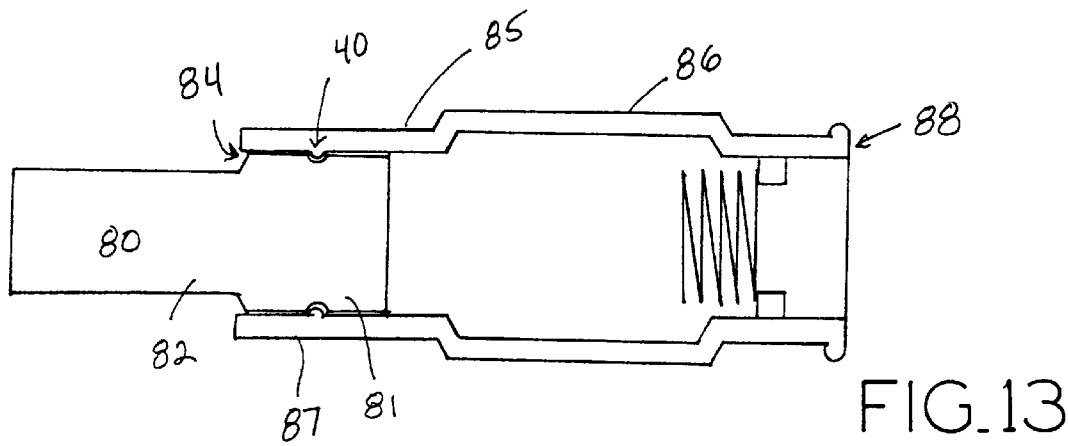
FIG. 13 depicts another embodiment of the device which includes a detent structure or mechanism that temporarily holds the shuttle in position.

FIG. 13 depicts another embodiment of the device in which includes a detent structure or mechanism that temporarily holds the shuttle in position. The device of FIG. 13 is somewhat similar to the device depicted in FIG. 11, except the shuttle 80 includes a wide portion 81 which includes the detent structure or mechanism 40 and a narrow portion 81. Also, the elongate body 85 includes a wide portion 86 which is between the detent structure or mechanism 40 and the mouthpiece 88. The device of FIG. 13 operates similar to the device of FIG. 11, except that when the detent structure or mechanism 40 releases shuttle 80, air is allowed to flow past shuttle 80 from an opening in the distal end 84 of the elongate body 85, as the wide portion 81 of the shuttle 80 enters the wide portion 86 of the elongate body 85 and the narrow portion 81 of the shuttle 80 enters the narrower portion 87 of the elongate body that includes the detent structure or mechanism 40.

It is noted that in the embodiments of the device depicted in FIGS. 2 and 3 the mouthpieces could be located on the opposite ends and a person could blow through the mouthpieces. The resulting pressure created in the person's mouth can help relieve inner ear pressure, particularly when the ambient pressure is greater than the inner ear pressure. Similarly, the mouthpieces of the other embodiments of the invention could be positioned on the opposite ends of the devices and used to blow into the devices to create pressure in a person's mouth.

Figure 14A:
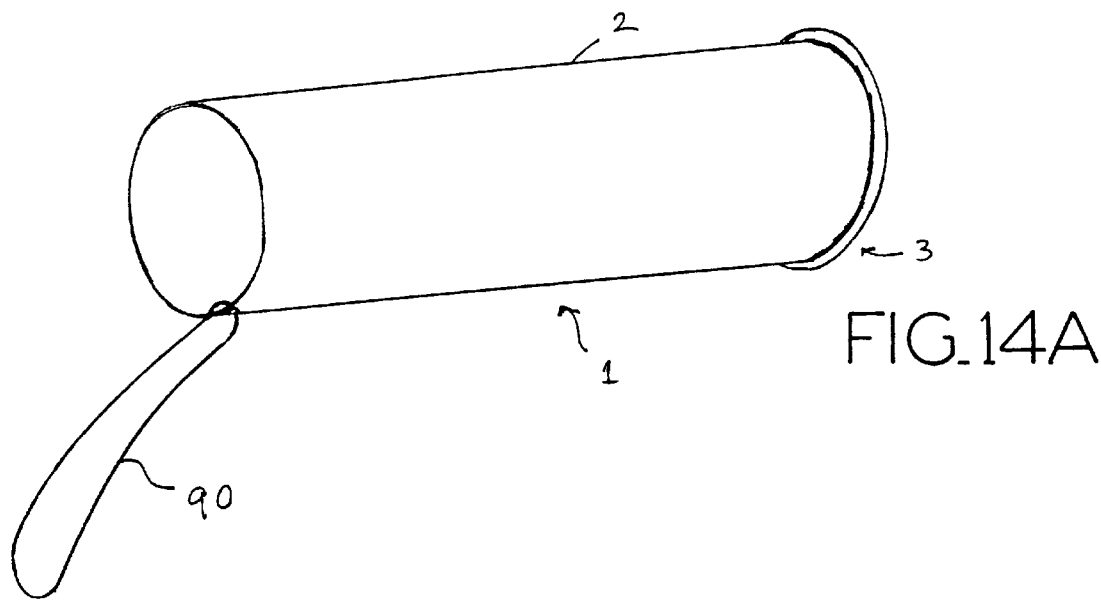
FIGS. 14a–14c depict various means which can be used to prevent the devices of the present invention from being swallowed or from choking a person.
Figure 14B:
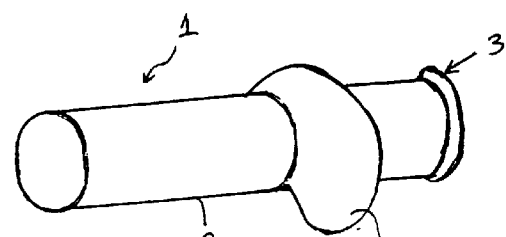
Figure 14C:
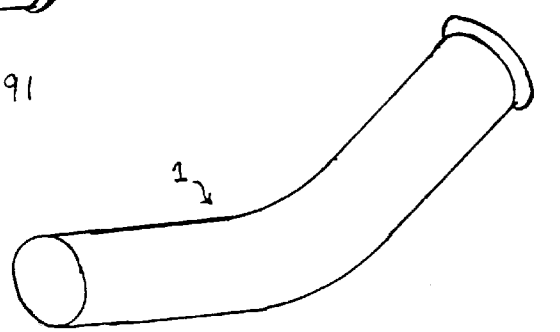

FIGS. 14a–14c depict various means which can be used to prevent the devices of the present invention from being swallowed.

FIG. 14a depicts a lanyard or tether 90 which can be attached to and end of a device according to the present invention. The lanyard or tether can be held or worn around a person's neck when the device is used to prevent swallowing or choking.

FIG. 14b depicts a structure 91 which is attached to the outer surface of the device near the mouthpiece 3. This structure can be similar to the structures on pacifiers which prevent babies from swallowing and choking on pacifiers.

FIG. 14c depicts an example of a device according to the present invention which has a shape that is other than linear which will prevent the device from being swallowed.

The devices of the present invention were developed to relieve inner ear pressure. Nevertheless, it is to be understood that the mouthpieces could be removed from the devices of the of the present invention, and the devices could be used to regulate pressures in different types of chambers, cavities, vessels, fluid systems, etc. For example, the devices of the present invention could be used to regulate internal pressures in reaction or reactor chambers. The unique rate or manner in which the devices of the present invention are capable of regulating pressure can be beneficial in reactions and processes which are pressure dependent.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as set forth in the appended claims.

What is claimed is:

1. A device for relieving inner ear pressure which comprises:
   a hollow elongate body having a mouthpiece on a first end thereof, and a cylindrical inner hollow portion;
   a movable member located in the cylindrical inner hollow portion of the hollow elongate body and defining a movable wall of a first chamber that extends between the movable member and the mouthpiece, movement of the movable member in the hollow elongate body being effected by pressure changes in the first chamber, the movable member having a cylindrical shape and includes at least one axial groove; and
   means for regulating pressure in the first chamber when a person applies a pressure change to the first chamber through the mouthpiece.

2. A device for relieving inner ear pressure according to claim 1, wherein the means for regulating pressure in the first chamber comprises a detent mechanism which cooperates between the elongate body and the movable member.

3. A device for relieving inner ear pressure according to claim 2, wherein a portion of the movable member extends beyond the hollow elongate body.

4. A device for relieving inner ear pressure according to claim 3, wherein the hollow elongate body includes a cross-sectional shape that has a wider portion between the detent mechanism and the mouthpiece.

5. A device for relieving inner ear pressure which comprises:
   a first hollow body member having a side wall and a mouthpiece on one end;
   a second body member telescopically coupled to the first hollow body member and having a wall which defines a wall of a chamber within the first hollow body member; and
   a detent mechanism formed on a portion of the side wall of the first hollow body and on a portion of the second hollow body which detent mechanism cooperates between the first hollow body member and the second body member to secure the relative positions therein, the detent mechanism further releasing and allowing the second body member to move axially with respect to the first hollow body member when a pressure change occurs in the chamber.

6. A device for relieving inner ear pressure according to claim 5, wherein the first hollow body member includes a cross-sectional shape that has a wider portion between the detent mechanism and the mouthpiece.

7. A device for relieving inner ear pressure according to claim 6, wherein the second body member includes at least one axial groove.

8. A device for relieving inner ear pressure according to claim 6, wherein the second body member includes a cross-sectional shape that is wider at an end that includes the detent mechanism and narrower at an opposite end.

9. A method of relieving inner ear pressure which comprises:
   providing an hollow elongate member having a mouthpiece on one end, a movable member that is received therein and defines a first chamber that extends between the movable member and the mouthpiece, and means for regulating pressure in the first chamber when a person applies a pressure change to the first chamber through the mouthpiece;
   positioning the mouthpiece in the mouth of a person experiencing a pressure difference between their inner ear pressure and ambient pressure;
   having the person apply a pressure change to the first chamber through the mouthpiece; and
   allowing the means for regulating pressure in the first chamber regulate the pressure therein to thereby relieve the pressure difference between the person's inner ear pressure and the ambient pressure.

10. A method for relieving inner ear pressure according to claim 9, wherein the means for regulating pressure in the first chamber causes a steady change in pressure.

11. A method for relieving inner ear pressure according to claim 9, wherein the means for regulating pressure in the first chamber causes an abrupt change in pressure.

12. A method for relieving inner ear pressure according to claim 9, wherein the means for regulating pressure in the first chamber causes a release of pressure.

13. A device for regulating pressure which comprises:
   a hollow body having an open end, and a cylindrical inner hollow portion;
   a movable member located in the cylindrical inner hollow portion of the hollow body and defining a movable wall of a chamber that extends between the movable member and the open end, wherein movement of the movable member within the hollow body is effected by pressure changes in the chamber, the movable member having a cylindrical shape and includes at least one axial groove; and
   means for regulating pressure in the first chamber when a pressure change is applied to the chamber through the open end, the means for regulating pressure comprising structure which controls movement of the movable member.

* * * * *